United States Patent
Olsson et al.

(10) Patent No.: US 10,456,388 B2
(45) Date of Patent: Oct. 29, 2019

(54) ANTIHISTAMINE FOR USE IN TREATMENT OF BREAST CANCER

(71) Applicant: BELINA PHARMA AB, Helsingborg (SE)

(72) Inventors: Hakan Olsson, Lund (SE); Rickard Einefors, Karlskoga (SE)

(73) Assignee: Belina Pharma AB, Helsingborg (SE)

( * ) Notice: Subject to any disclaimer, the term of this patent is extended or adjusted under 35 U.S.C. 154(b) by 0 days.

(21) Appl. No.: 15/544,575

(22) PCT Filed: Jan. 19, 2016

(86) PCT No.: PCT/EP2016/051000
§ 371 (c)(1),
(2) Date: Jul. 19, 2017

(87) PCT Pub. No.: WO2016/116438
PCT Pub. Date: Jul. 28, 2016

(65) Prior Publication Data
US 2018/0008588 A1   Jan. 11, 2018

(30) Foreign Application Priority Data
Jan. 19, 2015   (SE) ...................................... 1550036

(51) Int. Cl.
A61K 31/4545   (2006.01)
A61K 31/4515   (2006.01)
A61K 45/06     (2006.01)

(52) U.S. Cl.
CPC ...... *A61K 31/4545* (2013.01); *A61K 31/4515* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2002/0193371 A1 | 12/2002 | Telerman et al. | |
| 2003/0087900 A1* | 5/2003 | Telerman | A61K 31/138 514/225.2 |
| 2004/0072824 A1 | 4/2004 | Telerman et al. | |
| 2006/0166960 A1 | 7/2006 | Aslanian et al. | |
| 2010/0135956 A1 | 6/2010 | Gant et al. | |
| 2013/0263297 A1* | 10/2013 | Chu | A61K 39/39558 800/10 |

FOREIGN PATENT DOCUMENTS

| | | |
|---|---|---|
| CN | 103044395 A | 4/2013 |
| CN | 104292211 A | 1/2015 |
| RU | 2490028 C1 | 8/2013 |
| WO | 1994/018961 A1 | 9/1994 |
| WO | 2003/039526 A1 | 5/2003 |
| WO | 2004/080445 A1 | 9/2004 |
| WO | 2014/018563 A2 | 1/2014 |

OTHER PUBLICATIONS

Burke et al., Inhibition of constitutively active Stat3 suppresses growth of human ovarian and breast cancer cells, Oncogene (2001) 20, 7925-7934.*
Döbbeling, Udo et al., "The antihistamines clemastine and desloratadine inhibit STAT3 and c-Myc activities and induce apoptosis in cutaneous T-cell lymphoma cell lines," Experimental Dermatology. Feb. 2013, vol. 22 Issue 2, p. 119-124. 6p. 4 Graphs.*
Gordon, "The increasing efficacy of breast cancer treatment," Clin Oncol (R Coll Radiol). 1997;9(5):338-42.*
Ratner, "Comparison of once-daily ebastine 20 mg, ebastine 10 mg, loratadine 10 mg, and placebo in the treatment of seasonal allergic rhinitis. The Ebastine Study Group," J Allergy Clin Immunol. Jun. 2000;105(6 Pt 1):1101-7.*
Clarinex Dosage Instructions, Dec. 2001.*
Seiler et al., "Adverse Event Management of Oral Mucositis in Patients with Breast Cancer," Breast Care Apr. 2014; 9(4): 232-237.*
Booth et al., "Chemotherapy-induced nausea and vomiting in breast cancer patients: a prospective study," J Support Oncol. Sep. 2007; 5(8):374-380 (Abstract).*
International Search Report for corresponding International Application No. PCT/EP2016/051000 dated Apr. 4, 2016.
Written Opinion of the International Searching Authority for corresponding International Application No. PCT/EP2016/051000 dated Apr. 4, 2016.
Brandes et al., "Stimulation of Malignant Growth in Rodents by Antidepressant Drugs at Clinically Relevant Doses", Cancer Research, vol. 52, Jul. 1, 1992, pp. 3796-3800.
Carter, "New Global Survey Shows an Increasing 5 Cancer Burden", American Journal of Nursing, vol. 114, No. 3, Mar. 2014, p. 17.
Hemminki et.al., "Risk of cancer in patients with medically diagnosed hay fever or allergic rhinitis", International Journal of Cancer, vol. 135, 2014, pp. 2397-2403.
Nadalin et al., "Antihistamine Use and Breast Cancer Risk", International Journal of Cancer, vol. 106, 2003, pp. 566-568.
Selby et.al., "Screening Prescription Drugs for Possible Carcinogenicity: Eleven to Fifteen Years of Follow-up", Cancer Research, vol. 49, Oct. 15, 1989, pp. 5736-5747.
Martin et al., "Mast cell histamine promotes the immunoregulatory activity of myeloid-derived suppressor cells", Journal of Leukocyte Biology, vol. 96, Jul. 2014, pp. 151-159.
Office Action in corresponding Swedish Application No. 1550036-6 dated Aug. 14, 2015.
Brades et al., "Enhanced Cancer Growth in Mice Administered Daily Human-Equivalent Doses of Some H1-Antihistamines: Predictive In Vitro Correlates", Journal of the National Cancer Institute, vol. 86, No. 10, May 18, 2994, pp. 770-775.

* cited by examiner

*Primary Examiner* — Jared Barsky
(74) *Attorney, Agent, or Firm* — Renner, Otto, Boisselle & Sklar, LLP

(57) ABSTRACT

Disclosed herein is desloratadine or ebastin for use in treatment of a patient diagnosed with breast cancer. Also disclosed is desloratadine or ebastin for use in treatment of a patient diagnosed with a cancer type susceptible to immunotherapy.

9 Claims, 4 Drawing Sheets ns supplies,
ANTIHISTAMINE FOR USE IN TREATMENT OF BREAST CANCER

This application is a national phase of International Application No. PCT/EP2016/051000 filed Jan. 19, 2016 and published in the English language, and claims priority to Swedish Application No. 1550036-6 filed Jan. 19, 2015.

FIELD OF THE INVENTION

This invention pertains in general to the field of breast cancer treatment. More particularly the invention relates to a medicament for breast cancer treatment.

BACKGROUND OF THE INVENTION

It is known that breast cancer is one of the more common cancer types for women, and affects one in eight women during their lives. Risk factors for breast cancer include, gender, age, genes, personal factors and other risks such as being overweight, using hormone replacement therapy (also called menopausal hormone therapy), taking birth control pills, drinking alcohol, not having children or having your first child after age 35 or having dense breasts.

Symptoms of breast cancer may include a lump in the breast, a change in size or shape of the breast or discharge from a nipple. Breast self-exam and mammography can help find breast cancer early when it is most treatable. The treatment of primary breast cancer usually consists of surgery, often followed by adjuvant therapy (radiotherapy, chemotherapy, hormonal treatment, etc.).

Different types of treatment are available for patients with breast cancer. Most patients with breast cancer have surgery to remove the cancer from the breast, and several different surgical procedures exist for breast cancer removal. Other treatments include radiation therapy, a cancer treatment that uses high-energy x-rays or other types of radiation to kill cancer cells or keep them from growing. Chemotherapy is a cancer treatment that uses drugs to stop the growth of cancer cells, either by killing the cells or by stopping them from dividing. Hormone therapy is a cancer treatment that removes hormones or blocks their action and stops cancer cells from growing. Targeted therapy is a type of treatment that uses drugs or other substances to identify and attack specific cancer cells without harming normal cells, using for example monoclonal antibodies and tyrosine kinase inhibitors.

The 2014 World Cancer Report from WHO (The World health organization) reports that breast cancer is the second most common cancer worldwide, accounting for just over 1 million new cases annually. It states that in 2000 (the last year for which global data exists) about 400,000 women died from breast cancer, representing 1.6 percent of all female deaths. The proportion of breast cancer deaths was far higher in the rich countries (2 percent of all female deaths) than in economically poor regions (0.5 percent). Thus, breast cancer is strongly related to the Western lifestyle. As developing countries succeed in achieving lifestyles similar to Europe, North America, Australia, New Zealand and Japan, they will also encounter much higher cancer rates, particularly cancers of the breast. Recent data supports this prediction and show a 20% increase in breast cancer from 2008 to 2012. (Carter D. "New global survey shows an increasing cancer burden". Am J Nurs. 2014 March; 114(3):17).

Thus, there is a strong need for new types of treatment for breast cancer. While new treatment should aim at curing breast cancer, it would also be beneficial to improve the prognosis for a patient diagnosed with breast cancer or to increase the survival time for a patient diagnosed with breast cancer.

SUMMARY OF THE INVENTION

It is an object of the present invention, considering the disadvantages mentioned above, to provide a treatment of a patient diagnosed with breast cancer to improve the prognosis and increase the breast cancer related survival time of the patient.

These and other objects, which will appear from the following description, have now been achieved by a H1 receptor antihistamine for use in treatment of breast cancer, the H1 receptor antihistamine being desloratadine or ebastin.

The breast cancer is selected from the group consisting of positive and negative ER, PR, her2 breast cancer molecular subtypes, and invasive breast carcinomas. Alternatively, it is selected from the group consisting of positive and negative ER invasive breast carcinomas.

The treatment is continuous for at least 50 days, preferably at least 100 days and most preferably at least 400 days. Said treatment seeks to improve the prognosis for a patient diagnosed with breast cancer and/or seeks to increase the survival time for a patient diagnosed with breast cancer.

The daily dose of the H1 receptor antihistamine corresponds to the defined daily dose (DDD). When the H1 receptor antihistamine is desloratadine, the dose of the desloratadine is between 2.5 to 45 mg per day, preferably between 5 to 20 mg per day, most preferably 5 mg per day. When the H1 receptor antihistamine is ebastin, the dose of the ebastin is between 2.5 to 100 mg per day, preferably between 5 to 40 mg per day, most preferably 10 mg per day.

The use in treatment as described above, wherein the patient is not diagnosed with a seasonal allergic condition, or wherein the patient is perioperational, or wherein the patient is treated with radiotherapy, chemotherapy and/or hormonal treatment.

Also provided is a H1 receptor antihistamine for use in treatment of a cancer type susceptible to immunotherapy.

DESCRIPTION OF EMBODIMENTS

The following terms are employed herein:
AH Antihistamine
BR Breast Cancer
CI Confidence Intervals
ER Estrogen Receptor
HR Hazard Ratios
PR Progesterone Receptor
HER2 Human Epidermal Growth Factor Receptor 2

Database mining has proven a very powerful tool for finding unseen trends in treatment results. The Swedish Drug Register contains data on pharmaceuticals, supplies, and food taken prescription or equivalent in pharmacy from 1999 onwards. The number of prescriptions is almost 100 million a year. The register is updated with new information every month. The Swedish Cancer Registry was founded in 1958 and covers the entire population of Sweden. Approximately 50 000 malignant cases of cancer is registered every year in Sweden. It is compulsory for every health care provider to report newly detected cancer cases to the registry. A report has to be sent for every cancer case diagnosed at clinical-, morphological-, other laboratory examinations as well as cases diagnosed at autopsy. Thus, these registers provide a very good foundation for database mining seen from an international standard.

The study, underlying the present invention, uses material spanning over 8 years from these national registries and others, with no inclusion bias. The registries used are of good quality with full medical records from 2005, being a great indicator of drug usage, especially for persons with multiple prescriptions of the same drug.

Whilst looking for treatment relating to survival improvement of breast cancer patients, the present inventors found the surprising result that treatment using H1 receptor antagonists, especially desloratadine or ebastin, has a positive effect on breast cancer survival, as can be seen in FIGS. 1 to 3.

Using an extended breast cancer material of all cases from the Swedish Cancer Registry 2000-2013 (n=103 500 cases) linking the data with the Drug Prescription Registry a replication study was carried out. The data from this extended study can be found in Tables 10 and 11. With the larger set of data, the effect for each individual antihistamine becomes more pronounced. It is evident that an overall effect for better breast cancer survival is present for desloratadine and ebastine. Table 11 summarizes this effect for desloratadine. Looking at the years before 2009 the survival is greatly improved for desloratadine users compared with non users HR=0.63.

Table 10 further shows that the H1 receptor antagonists clemastine and cetirizine negatively affects BC survival (HR=1.12 and HR=1.28), highlighting the clear difference between studies employing real patient data and in vitro studies. In the in vitro trials described in US 2004/0072824 A1, it is suggested that clemastine has in vitro cytotoxic effects for cancer cell lines. Similary, WO 2004/080445 A1, suggests that clemastine has in vitro cytotoxic effects and that both clemastine and cetirizine can be used for inhibiting growth of cancer cells. The present real patient data shown in table 10, however shows that the possible general cytotoxic effect of clemastine and cetirizine does not provide any improved BC survival rate in vivo. On the contrary, use of these anti-histamines seemingly, lowers the BC survival rate.

Thus in a first embodiment of the invention, a H1 receptor antihistamine being desloratadine or ebastin is used for treatment of breast cancer.

This was surprising since antihistamines are structurally similar to DPPE, a tamoxifen derivative known to promote tumor growth. They have historically been seen as a risk factor for breast cancer, and animal experiments have linked certain antihistamines (Brandes L J et al. "Enhanced cancer growth in mice administered daily human-equivalent doses of some H1-antihistamines: predictive in vitro correlates". J Nat Cancer Inst 1994; 86:770-5.) and antidepressants (Brandes, L J et al. "Stimulation of malignant growth in rodents by antidepressant drugs at clinically relevant doses." Cancer Res 1992; 52:3796-800) with enhanced tumor growth in mice.

However, few epidemiologic studies examining antihistamine have been performed. These studies have aimed at evaluating the breast cancer risk. They have however not indicated an increased risk of breast cancer. There are even statistical studies that conclude that women who use antihistamines are not at a greater breast cancer risk than those who do not (Nadalin, V. et al. "Antihistamine use and breast cancer risk". Int. J. Cancer: 106, 566-568, (2003)). Thus, the art is inconclusive.

Looking at individual H1 receptor antagonists, the study can present the clear benefits from antihistamine treatment for women with breast cancer (BC) using klemastine, loratadine, desloratadine, ebastin and fexofenadine in an ever-use model. As can be seen from FIGS. 2 and 3, these women had a clear, statistically significant, longer BC specific survival compared to controls, especially from desloratadine and ebastin treatment.

The positive effect is seen for different breast cancer molecular subtypes, such as both positive and negative ER, as can be seen in tables 8 and 9. This is equally surprising, since ER negative subtypes are considered very hard to treat. It is however very likely conceivable that the effect also pertain to other breast cancer molecular subtypes, such as PR and her2 subtypes, although the effect on these subgroups cannot be singled out from the data registries. In one embodiment of the present invention, the breast cancer includes positive and negative ER invasive breast carcinomas. In another embodiment of the present invention, the breast cancer includes positive and negative ER, PR, her2 breast cancer molecular subtypes, and invasive breast carcinomas.

The improvement seen for breast cancer patients using the H1 receptor antihistamines being desloratadine or ebastine include improved prognosis as well as increase in survival rate. Thus, in one embodiment of the present invention, the treatment seeks to improve the prognosis for a patient diagnosed with breast cancer. In another embodiment of the present invention, the treatment seeks to increase the survival time for a patient diagnosed with breast cancer.

H1-antihistamines are clinically used in the treatment of histamine-mediated allergic conditions. The term "antihistamine" refers to H1 antagonists, also known as H1-receptor antagonists and H1-antihistamines, which serve to reduce or eliminate effects mediated by histamine, an endogenous chemical mediator released during allergic reactions.

To rule out the possibility that an allergy of a patient has a role in the positive effect on breast cancer survival when using H1 receptor antagonists, data analysis from out- and inpatient with diagnosis of allergy showed that use of antihistamines still improved survival diagnosis (not shown). In fact, literature investigating allergy and cancer instead suggest that the risk for individual cancers such as breast-prostate and kidney cancers is increased by allergic conditions (Hemminki et. al. "Risk of cancer in patients with medically diagnosed hay fever or allergic rhinitis". Int. J. Cancer: 135, 2397-2403 (2014)).

In one embodiment of the present invention, the H1 receptor antihistamine being desloratadine or ebastine is for use in treatment of a patient diagnosed with breast cancer but not diagnosed with a seasonal allergic condition. In another embodiment of the present invention, the H1 receptor antihistamine being desloratadine or ebastine is for use in treatment of a patient diagnosed with breast cancer but not diagnosed with an allergic condition, such as allergic conditions for which H1 receptor antihistamine treatment typically is administered continuously for 6 months or longer.

To reduce the survival bias that comes from treatment starting after BC diagnosis, a comparative late entry model is also used in the study of the invention. This takes into account additional study subjects who enter during the study period. For there late entries, there is a possibility that the delayed entries may have different hazards compared to the other standard subjects. As can be seen from FIGS. 4 and 5, women joining the study as late entries, using loratadine, desloratadine and ebastin had a statistically significant longer BC specific survival, compared to controls. Similarly, women joining the study as late entries, using cetirizine, klemastine and fexofenadine had a non-statistically significant longer BC specific survival compared to controls.

Desloratadine, loratadine or ebastin are all second-generation H1-antihistamines. Second-generation H1-antihistamines are newer drugs that are more selective for peripheral H1 receptors as opposed to the central nervous system H1 receptors and cholinergic receptors. They are all very polar compounds, which mean that they do not cross the blood-brain-barrier (BBB) and will act mainly outside the central nervous system.

There are many potential mechanisms to mediate the effect observed. The effect is mostly pronounced for desloratadine. This could connect to the fact that it has the strongest affinity to the H1 receptor. It also seems to have a greater effect on the immune system by affecting cytokine levels. Further, desloratadine has a much higher volume of distribution than most other H1 antagonists which results in a higher tissue distribution. This, coupled with the long half-life for desloratadine would mean a daily desloratadine therapy would provide a fairly complete blocking of basal H1 signaling in almost all tissues and in all organs, such as in tumors.

In this study, the drug usage is estimated based on drug prescriptions. This information reflects usage fairly accurate, especially for persons with multiple prescriptions. A confounding factor is the possibility of off the counter purchase of cetirizine and loratadine, though this should only dilute any seen effects. Desloratadine and klemastine however, were both prescription drugs, during the time of this study.

Thus, in an embodiment of the present invention, the daily dose of the H1 receptor antihistamine being desloratadine or ebastine corresponds to the defined daily dose (DDD). The DDD is a statistical measure of drug consumption, defined by the World Health Organization (WHO).

FIG. 6 shows the benefit of a longer treatment term at a standard dose regime. It can clearly be established that women using desloratadine for 400 days or longer shows a clearly better effect of the treatment compared to those who have been using desloratadine for less than 400 days. In an embodiment of the present invention, the treatment is continuous for at least 50 days, such as at least 100 days. The treatment may even be continuous for at least 400 days.

FIG. 7 establishes the treatment period in relation to the time of the breast cancer diagnosis. For women using desloratadine only before the BC diagnosis, no positive effects on breast cancer survival rate can be established. However, for the group of women using desloratadine only after the BC diagnosis, clear positive effects can be shown. For women using desloratadine both before and after the BC diagnosis, similar positive effects can be seen, however this group was not large enough for establishing statistical significance.

This study shows a benefit from antihistamine treatment in normal dose regimes, but other dose regimes are equally possible, for instance a higher dose for perioperational treatment.

In one embodiment of the present invention, a H1 receptor antihistamine being desloratadine or ebastine is used in perioperational treatment of a patient diagnosed with breast cancer.

Possible benefits of a higher dose regime is also suggested by FIG. 7, where the group using desloratadine both before and after the BC diagnosis shows an immediate a positive effect, suggesting the that a certain initial treatment period is required for the treatment to become most effective, which might be shortened by a larger dose regimen.

Thus, in one embodiment of the present invention, the dose of the desloratadine is between 2.5 to 45 mg per day, preferably between 5 to 20 mg per day, most preferably 5 mg per day. Multi dose studies with 45 mg per day of desloratadine did not show any further clinical side effects (FASS, Swedish Medicines Compendium for healthcare professionals). Thus, in one further embodiment, high doses of desloratadine are administered, between 45 to 250 mg per day, preferably between 85 to 150 mg per day most preferably 100 mg per day.

In one embodiment of the present invention, the dose of the ebastin is between 2.5 to 100 mg per day, preferably between 5 to 40 mg per day, most preferably 10 mg per day. Multi dose studies with 100 mg per day of ebastin did not show any further clinical side effects (FASS, Swedish Medicines Compendium for healthcare professionals). Thus, in one further embodiment, high doses of ebastin are administered, between 100 to 500 mg per day, preferably between 150 to 300 mg per day most preferably 200 mg per day.

A minor part of the prescriptions of antihistamines are prescribed to ease the side effects of chemotherapy. How this affects the result of this study is unknown, as we do not have access to chemotherapy data. In the record however, it seems that klemastine is the drug of choice for this purpose. However, a large number of the BC patients of the study, have undergone conventional BC treatment alongside the use of H1 receptor antagonists. Thus, the positive effect of co-treatment with H1 receptor antagonists together with conventional BC treatment has been clearly established.

Thus, in one of the present invention there is provided a H1 receptor antihistamine being desloratadine or ebastine for use in the co-treatment of a patient diagnosed with cancer, wherein said co-treatment further includes treatment with radiotherapy, chemotherapy, hormonal treatment.

In a further embodiment of the present invention, there is provided a H1 receptor antihistamine being desloratadine or ebastine and a chemotherapeutic agent and/or a hormonal agent for use in the co-treatment of a patient diagnosed with cancer.

In yet another embodiment of the present invention, a pharmaceutical formulation comprising a H1 receptor antihistamine being desloratadine or ebastine and a chemotherapeutic agent is provided. The chemotherapeutic agent of the pharmaceutical formulation may be an anthracycline, taxane or a platinum agent.

In yet another embodiment of the present invention, a pharmaceutical formulation comprising a H1 receptor antihistamine being desloratadine or ebastine and a hormonal agent is provided. The hormonal agent may be tamoxifen, toremifene, fulvestrant or an aromatase inhibitor.

Immunotherapy of cancer has recently had astonishing success especially by use of antibodies directed against T-cell regulating targets. In patients with metastatic melanoma long time survival has been achieved in 20% of the patients and it could be possible that a subgroup is cured. Also subgroups of patients with triple negative or Her2-neu positive breast cancer are thought to be candidates for immunotherapy. Studies whether patients with other tumor types, such as kidney cancer and lung cancer, also could be susceptible to immunotherapy are underway. Preliminary data presented at large international conferences suggest interesting patient responses to therapy. It is therefore conceivable that immunotherapy may be successful in minor subgroups of most cancer types. If the effect seen here for antihistamines is due to an immunological mechanism, other tumor types than breast cancer, such as malignant melanoma, breast cancer, kidney cancer, lung cancer, hematopoetic malignancies, malignant lymphoma, prostate cancer, gliomas or cervical cancer, may in a similar manner show positive survival effects.

In one embodiment of the present invention, there is provided a H1 receptor antihistamine being desloratadine or ebastine for use in treatment of a cancer type susceptible to immunotherapy.

About 5% to 10% of breast cancer cases are thought to be hereditary, meaning that they result directly from gene defects inherited from a parent. The most well known cause of hereditary breast cancer is an inherited mutation in the BRCA1 and BRCA2 genes. Normally, these genes help prevent cancer by making proteins for error-free DNA-repair process that keep the cells from growing abnormally. Other gene mutations, such as ATM, TP53, CHEK2, PTEN, CDH1, STK11 or PALB2, are also connected to inherited breast cancers. There are also several other known risk factors, such as non-cancerous (benign) breast conditions like non-proliferative lesions or proliferative lesions (with or without atypia), which may lead to a 5 to 10-fold increase in risk of breast cancer. Other detected changes (i.e. abnormal cells) in the breast tissue, such as lobular carcinoma in situ (LCIS) and ductal carcinoma in situ (DCIS), increase the risk for breast cancer or, in the case of DCIS, will eventually become cancer.

According to an embodiment, there is provided a H1 receptor antihistamine being desloratadine or ebastine for use in pre-treatment, i.e. prophylactic treatment for women with high risk factors for or developing breast cancer.

A woman diagnosed with breast cancer in one breast has a 3- to 4-fold increase in risk of developing a new cancer in the other breast or in another part of the same breast, differing from a recurrence (return) of the first cancer.

According to an embodiment, there is provided a H1 receptor antihistamine being desloratadine or ebastine for use in pre-treatment, i.e. prophylactic treatment for women with cancer in one breast with high risk factors for or developing a new cancer in the same breast or in another part of the other breast.

Evidently, a H1 receptor antihistamine being desloratadine or ebastine may also be used for the manufacture of a medicament for use in such treatment as disclosed herein, e.g. treatment of breast cancer. Similarly, a H1 receptor antihistamine being desloratadine or ebastine may obviously also be used in method for treating such diseases and disorders as have been disclosed herein e.g. treatment of breast cancer. Such a method includes the step of administering an effective amount of the H1 receptor antihistamine being desloratadine or ebastine to a subject in need for such treatment.

In the context of the present specification, the term "therapy" and "treatment" includes prevention or prophylaxis, unless there are specific indications to the contrary. The terms "therapeutic" and "therapeutically" should be construed accordingly.

According to an embodiment, treatment does also encompass pre-treatment, i.e. prophylactic treatment.

According to an embodiment, the term "prophylaxis" or "prophylactic" includes primary prophylaxis, secondary prophylaxis, tertiary prophylaxis or periodic prophylaxis, unless there are specific indications to the contrary. Primary prophylaxis refers to the preventive treatment of an initial disease. Secondary prophylaxis refers to reducing the incidence of recurrence or reactivation of a pre-existing disease. Tertiary prophylaxis refers to continuous treatment started after the onset of a disease to mitigate further damage. Periodic prophylaxis refers to periodic prophylactic treatment given for shorter periods of time. For instance, a H1 receptor antihistamine being desloratadine or ebastine used in perioperational treatment may be used a secondary prophylaxis for reducing the incidence of recurrence or reactivation of a pre-existing breast cancer.

Thus, in one embodiment of the present invention, treatment does relate to primary prophylaxis, secondary prophylaxis, tertiary prophylaxis or periodic prophylaxis.

Although the present invention has been described above with reference to (a) specific embodiment(s), it is not intended to be limited to the specific form set forth herein. Rather, the invention is limited only by the accompanying claims and, other embodiments than the specific above are equally possible within the scope of these appended claims, e.g. different than those described above.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

Materials and Methods

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

Figure 1:
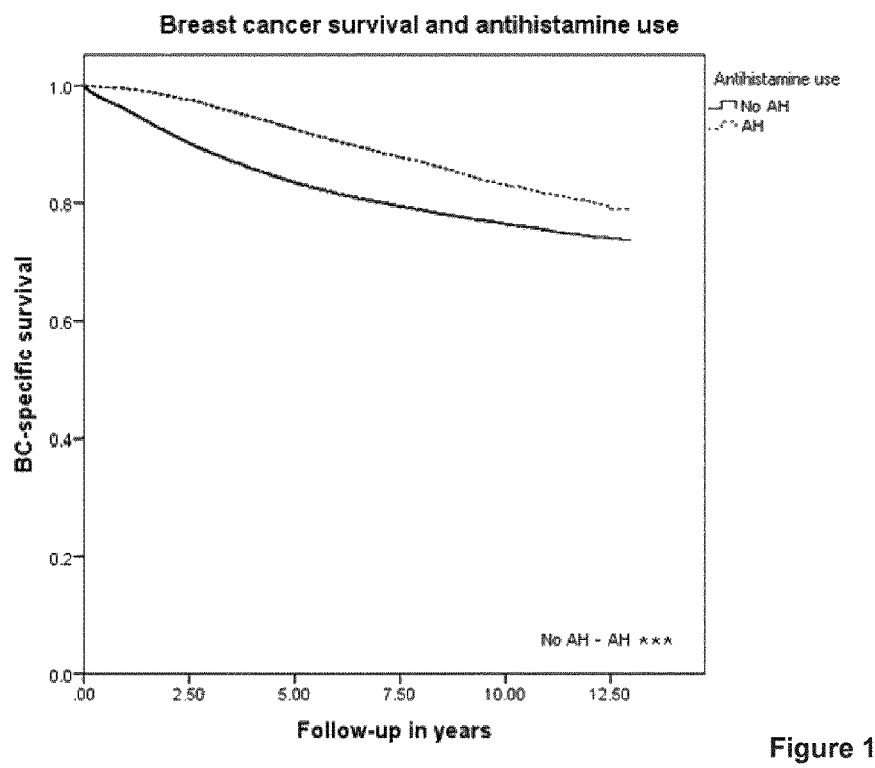
FIG. 1 is a graph showing breast cancer survival according to ever-use of antihistamines for allergic purposes.

A cohort consisting of all Swedish women, without a previous cancer, diagnosed with BC from 2000 through 2008 was used. The study was approved by an ethical board in Sweden. Date of birth, date of BC diagnosis and TNM-stage was gathered from the Swedish Cancer Registry. The women's pharmaceutical records with start from the 1st of Jul. 2005 were gathered from the Swedish Pharmaceutical Register. Date of death was gathered from the Swedish Population Register up until the 31st of Dec. 2013. Cause of death was also gathered from the Swedish Population Register, but was only available up to 31st of Dec. 2012. Women over 50 years of age at BC diagnosis were considered postmenopausal, whereas women under 50 were considered premenopausal. A group consisted of all women with a prescription of antihistamines for allergic purposes were created, and then also split into group according to which antihistamine that had been used the most. The control group consisted of all women without a prescription of an antihistamine for allergic purposes. In the ever-use model, all women who have had a prescription of antihistamines in the Swedish Pharmaceutical Register from the 1st of Jul. 2005 are included.

The stages of breast cancer is described using the American Joint Committee on Cancer (AJCC) TNM system. The TNM staging system classifies cancers based on their T, N, and M stages:

The letter T followed by a number from 0 to 4 describes the tumor's size and spread to the skin or to the chest wall under the breast. Higher T numbers mean a larger tumor and/or wider spread to tissues near the breast.

The letter N followed by a number from 0 to 3 indicates whether the cancer has spread to lymph nodes near the breast and, if so, how many lymph nodes are affected.

The letter M followed by a 0 or 1 indicates whether the cancer has spread to distant organs—for example, the lungs or bones.

The T-stage data was recoded into a variable set from 1 to 5, where 1-4 corresponded to the reported T-stage and for 5 missing T-stage. The N-stage data was recoded into a variable set from 0 to 4, where 0-3 corresponded to the reported N-stage and 4 for missing N-stage. M-stage was recoded into a variable of either 0 and 2, where 0 corresponded to the reported 0 M-stage and 2 missing M-stage. All this data came from the Swedish Cancer Registry.

Since ever-use of antihistamines for allergic purposes was investigated, the majority of the users bought their prescribed antihistamines after BC diagnosis. It was decided to look at survival and hazard in two ways—by dividing the groups according to ever-use and secondly by using a late entry model to reduce the survival bias in the first model. In the late entry model all women with unknown N-status and all cases before 1st of Jul. 2005 was excluded to get a more precise result.

Using an extended breast cancer material of all cases from the Swedish Cancer Registry 2000-2013 (n=103 500 cases) linking the data with the Drug Prescription Registry a replication study was carried out. The data from this extended study are represented in tables 10 and 11.

Statistics

Statistical analyses were performed using IBM SPSS 22.0 and R studio v 0.98.983.

Univariate BC specific survival was estimated using Kaplan-Meier for a group combined of all antihistamine users and for each specific antihistamine group. The distribution was tested using the Log-rank test.

Hazard Ratios (HR) were calculated using cox proportional hazard. HR was calculated for each group of antihistamine users and adjustments were made for age at BC diagnosis (linear), T-stage (T1, T2, T3, T4, Missing), N-stage (N0, N1, N2, N3, Missing), M-stage (M0, M1, Missing). The multivariate analysis was also stratified for ER-status. HR were estimated with 95% confidence intervals (CI). Two-tailed p-values were used for all analyses. A p-value of less than 0.05 was regarded as statistically significant.

The late entry cox proportional hazard analyses done in R studio, HR was calculated for each group of antihistamine users and adjustments were made for age at BC diagnosis (linear), T-stage (T1, T2, T3, T4, Missing) and N-stage (N0, N1+). This analysis was also stratified for ER-status. HR were estimated with 97.5% confidence intervals (CI). Two-tailed p-values were used for all analyses. A p-value of less than 0.05 was regarded as statistically significant.

Results

This study included 47350 women with invasive BC. Patient characteristics can be seen in table 1. 18724 were included after 1st of Jul. 2005, when the Swedish Pharmaceutical Register began. Their patient characteristics can be seen in table 2. A replication study including of all BC cases from the Swedish Cancer Registry 2000-2013 (n=103 500 cases) is shown in table 10.

TABLE 1

Patient characteristics for women with divided into groups according to their main antihistamine used. The table includes all patients from 2000-2008.

| | | Main antihistamine | | | | | | |
|---|---|---|---|---|---|---|---|---|
| | | No AH 37573 | Cetirizine 3001 | Klemastine 2278 | Loratadine 2132 | Desloratadine 1895 | Ebastin 326 | Fexofenadine 145 |
| Age at BC diagnosis | Mean | 64.25 | 58.33 | 61.15 | 59.12 | 58.36 | 58.28 | 58.38 |
| Follow-up in years | Mean | 6.79 | 7.31 | 7.39 | 7.48 | 7.90 | 7.88 | 7.63 |
| Dead in BC | Yes | 20.2% | 18.0% | 13.8% | 11.7% | 7.1% | 6.7% | 9.0% |
| Menopause at BC diagnosis | Yes | 82.6% | 71.3% | 79.1% | 75.7% | 74.6% | 72.1% | 73.8% |
| T stage | 1 | 32.0% | 34.3% | 36.1% | 36.6% | 41.4% | 38.7% | 31.7% |
| | 2 | 20.2% | 23.1% | 21.8% | 23.3% | 18.6% | 21.2% | 24.1% |
| | 3 | 3.1% | 4.1% | 4.0% | 4.4% | 2.7% | 2.5% | 3.4% |
| | 4 | 2.3% | 1.6% | 1.4% | 1.4% | .8% | .9% | 2.1% |
| | Missing | 42.4% | 36.9% | 36.7% | 34.3% | 36.4% | 36.8% | 38.6% |
| N stage | 0 | 37.3% | 40.3% | 42.4% | 45.5% | 46.8% | 49.4% | 40.0% |
| | 1 | 16.2% | 19.5% | 18.7% | 18.9% | 15.5% | 13.2% | 18.6% |
| | 2 | .6% | 1.1% | 1.0% | 1.0% | .3% | .6% | .7% |
| | 3 | .3% | .5% | .3% | .2% | .2% | 0.0% | 1.4% |
| | Missing | 45.6% | 38.6% | 37.6% | 34.3% | 37.4% | 36.8% | 39.3% |

TABLE 1-continued

Patient characteristics for women with divided into groups according to their main antihistamine used. The table includes all patients from 2000-2008.

| | | Main antihistamine | | | | | | |
|---|---|---|---|---|---|---|---|---|
| | | No AH 37573 | Cetirizine 3001 | Klemastine 2278 | Loratadine 2132 | Desloratadine 1895 | Ebastin 326 | Fexofenadine 145 |
| M stage | 0 | 43.4% | 46.0% | 49.1% | 54.8% | 52.2% | 51.2% | 48.3% |
| | 1 | 1.9% | 1.6% | 1.3% | .8% | .8% | 0.0% | 1.4% |
| | Missing | 54.7% | 52.4% | 49.6% | 44.4% | 47.0% | 48.8% | 50.3% |

TABLE 2

Patient characteristics for women with divided into groups according to their main antihistamine used. The table includes all patients from 1st of Jul. 2005-31st of Dec. 2008.

| | | Main antihistamine | | | | | | |
|---|---|---|---|---|---|---|---|---|
| | | No AH 14192 | Cetirizine 1392 | Klemastine 1034 | Loratadine 1038 | Desloratadine 859 | Ebastin 140 | Fexofenadine 69 |
| Age at BC diagnosis | Mean | 64.62 | 58.99 | 61.57 | 59.36 | 59.34 | 57.92 | 58.83 |
| Follow-up in years | Mean | 5.00 | 5.17 | 5.13 | 5.46 | 5.48 | 5.54 | 5.20 |
| Dead in BC | Yes | 15.4% | 16.5% | 14.3% | 10.4% | 8.1% | 5.7% | 11.6% |
| Menopause at BC diagnosis | Yes | 82.5% | 71.8% | 77.5% | 75.3% | 74.5% | 70.7% | 73.9% |
| T stage | 1 | 47.1% | 43.4% | 47.0% | 46.0% | 56.8% | 52.9% | 44.9% |
| | 2 | 29.7% | 32.9% | 31.4% | 31.5% | 25.0% | 31.4% | 30.4% |
| | 3 | 4.4% | 5.5% | 6.1% | 6.2% | 3.7% | 2.1% | 5.8% |
| | 4 | 3.3% | 2.5% | 2.0% | 1.4% | .9% | 1.4% | 2.9% |
| | Missing | 15.5% | 15.7% | 13.4% | 14.9% | 13.5% | 12.1% | 15.9% |
| N stage | 0 | 55.1% | 54.1% | 56.8% | 56.6% | 61.8% | 65.0% | 50.7% |
| | 1 | 20.8% | 24.8% | 23.5% | 25.2% | 20.1% | 19.3% | 24.6% |
| | 2 | 1.2% | 1.8% | 2.1% | 1.3% | .6% | 1.4% | 1.4% |
| | 3 | .5% | 1.1% | .3% | .3% | .2% | 0.0% | 2.9% |
| | Missing | 22.4% | 18.2% | 17.3% | 16.6% | 17.2% | 14.3% | 20.3% |
| M stage | 0 | 61.4% | 60.3% | 65.3% | 69.2% | 67.6% | 71.4% | 59.4% |
| | 1 | 2.7% | 1.8% | 2.0% | .6% | 1.3% | 0.0% | 1.4% |
| | Missing | 35.9% | 37.9% | 32.7% | 30.3% | 31.1% | 28.6% | 39.1% |

Ever-Use Model

FIG. 1 shows the breast cancer survival according to ever-use of antihistamines for allergic purposes. N=9777 in the No AH group and N=37573 in the AH group.

Univariate Analyses

Figure 2:
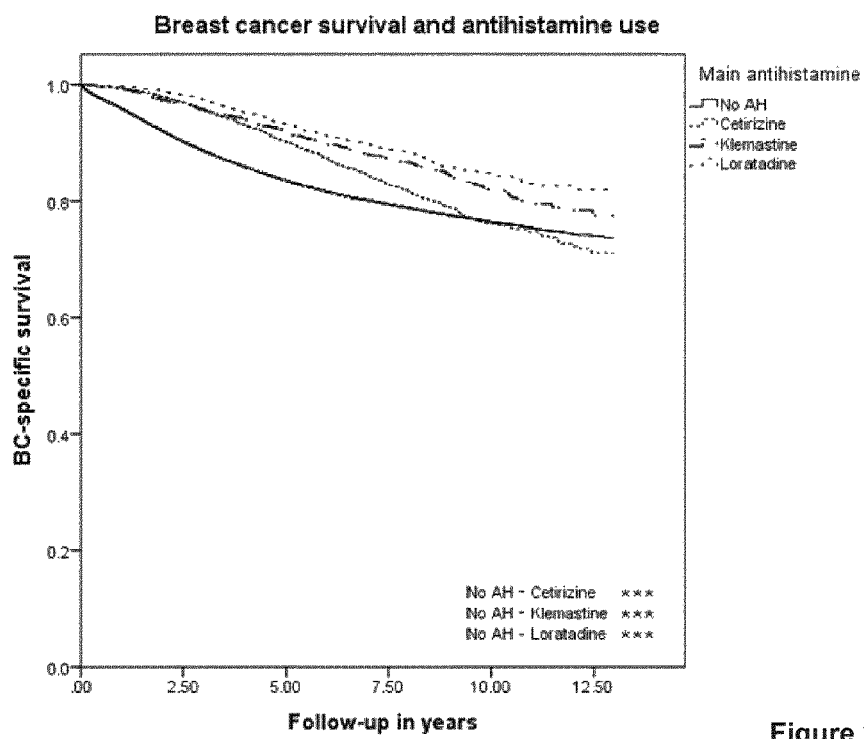
FIG. 2 is a graph showing breast cancer survival according to ever-use of antihistamines of Cetirizine, Klemastine and Loratadine.
Figure 3:
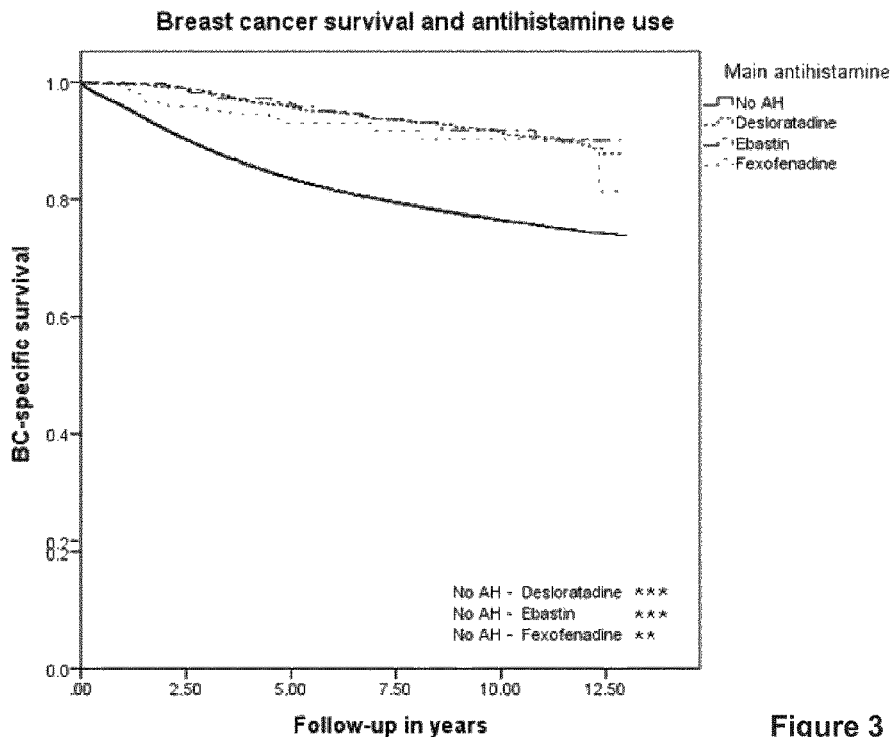
FIG. 3 is a graph showing breast cancer survival according to ever-use of antihistamines of Desloratadine, Ebastin and Fexofenadine.

Women using a H1 receptor antihistamine of any kind had a statistically significant longer BC specific survival, compared to controls. (FIG. 1) Women using klemastine, loratadine, desloratadine, ebastin and fexofenadine had a statistically significant longer BC specific survival, compared to controls. Women using cetirizine initially had a higher survival percentage compared to controls, but with time it became lower compared to controls. (FIGS. 2 and 3). FIG. 2 shows the breast cancer survival according to ever-use of antihistamines of Cetirizine, Klemastine and Loratadine. N=37573 in the No AH group, N=3001 in the Cetirizine group, N=2278 in the Klemastine group and N=2132 in the Loratadine group. FIG. 3 shows the breast cancer survival according to ever-use of antihistamines of Desloratadine, Ebastin and Fexofenadine. N=37573 in the No AH group, N=1895 in the Desloratadine group, N=326 in the Ebastin group and N=145 in the Fexofenadine group.

Multivariate Analyses

The HR for the combined group of antihistamine users adjusted for age at BC diagnosis and TNM was 0.70 (0.66-0.75) (Table 3).

TABLE 3

Cox proportional harzard Variables in the Equation

| | B | SE | Wald | df | Sig. | Exp(B) | 95.0% CI for Exp(B) | |
|---|---|---|---|---|---|---|---|---|
| | | | | | | | Lower | Upper |
| Age at BC diagnosis | .037 | .001 | 2005.719 | 1 | 0.000 | 1.037 | 1.036 | 1.039 |
| T1 | | | 1331.374 | 4 | .000 | Ref | | |
| T2 | .945 | .037 | 656.457 | 1 | .000 | 2.573 | 2.393 | 2.766 |
| T3 | 1.478 | .052 | 814.214 | 1 | .000 | 4.384 | 3.961 | 4.852 |

TABLE 3-continued

Cox proportional harzard Variables in the Equation

| | B | SE | Wald | df | Sig. | Exp(B) | 95.0% CI for Exp(B) Lower | Upper |
|---|---|---|---|---|---|---|---|---|
| T4 | 1.579 | .056 | 803.066 | 1 | .000 | 4.848 | 4.347 | 5.407 |
| T missing | .412 | .044 | 87.816 | 1 | .000 | 1.509 | 1.385 | 1.645 |
| N0 | | | 687.278 | 4 | .000 | Ref | | |
| N1 | .837 | .034 | 597.630 | 1 | .000 | 2.310 | 2.160 | 2.471 |
| N2 | .962 | .088 | 118.202 | 1 | .000 | 2.616 | 2.200 | 3.112 |
| N3 | 1.011 | .118 | 73.029 | 1 | .000 | 2.748 | 2.179 | 3.465 |
| N missing | .853 | .043 | 385.863 | 1 | .000 | 2.347 | 2.155 | 2.555 |
| M0 | | | 1030.324 | 2 | .000 | Ref | | |
| M1 | 1.514 | .050 | 933.373 | 1 | .000 | 4.546 | 4.125 | 5.009 |
| M missing | −.021 | .033 | .377 | 1 | .539 | .980 | .918 | 1.046 |
| Antihistamine use | −.353 | .031 | 133.427 | 1 | .000 | .702 | .661 | .746 |

Hazard ratios for women with ever-use of antihistamines compared to controls adjusted for age at breast cancer diagnosis and TNM-stage.

Table 4 shows HR for each group of antihistamine users adjusted for age at BC diagnosis and TNM. Women using desloratadine had a HR of 0.41 (0.35-0.49). Loratadine users had a HR of 0.64 (0.56-0.72). Cetirizine users had a HR of 0.97 (0.89-1.06) and Klemastine users had a HR of 0.69 (0.62-0.77). Ebastin users had a HR of 0.40 (0.27-0.61) and Fexofenadine users had a HR of 0.49 (0.29-0.85).

TABLE 4

Cox proportional harzard Variables in the Equation

| | B | SE | Wald | df | Sig. | Exp(B) | 95.0% CI for Exp(B) Lower | Upper |
|---|---|---|---|---|---|---|---|---|
| Age at BC diagnosis | .037 | .001 | 2009.883 | 1 | 0.000 | 1.037 | 1.036 | 1.039 |
| T1 | | | 1322.645 | 4 | .000 | Ref | | |
| T2 | .940 | .037 | 649.372 | 1 | .000 | 2.561 | 2.382 | 2.753 |
| T3 | 1.473 | .052 | 808.650 | 1 | .000 | 4.364 | 3.943 | 4.831 |
| T4 | 1.579 | .056 | 805.349 | 1 | .000 | 4.850 | 4.349 | 5.409 |
| T missing | .416 | .044 | 89.433 | 1 | .000 | 1.515 | 1.390 | 1.651 |
| N0 | | | 678.184 | 4 | .000 | Ref | | |
| N1 | .832 | .034 | 589.279 | 1 | .000 | 2.298 | 2.148 | 2.457 |
| N2 | .958 | .088 | 117.541 | 1 | .000 | 2.607 | 2.192 | 3.099 |
| N3 | .995 | .118 | 70.861 | 1 | .000 | 2.706 | 2.146 | 3.411 |
| N missing | .849 | .043 | 381.777 | 1 | .000 | 2.337 | 2.146 | 2.545 |
| M0 | | | 1030.468 | 2 | .000 | Ref | | |
| M1 | 1.508 | .049 | 929.330 | 1 | .000 | 4.517 | 4.100 | 4.977 |
| M missing | −.028 | .033 | .694 | 1 | .405 | .973 | .911 | 1.038 |
| No antihistamine | | | 206.497 | 6 | .000 | Ref | | |
| Cetirizine | −.030 | .045 | .447 | 1 | .504 | .970 | .889 | 1.060 |
| Klemastine | −.371 | .058 | 41.580 | 1 | .000 | .690 | .616 | .772 |
| Loratadine | −.453 | .065 | 49.183 | 1 | .000 | .636 | .560 | .722 |
| Desloratadine | −.889 | .087 | 104.341 | 1 | .000 | .411 | .347 | .488 |
| Ebastine | −.907 | .214 | 18.047 | 1 | .000 | .404 | .266 | .613 |
| Fexofenadine | −.709 | .278 | 6.520 | 1 | .011 | .492 | .286 | .848 |

Hazard ratios for women with ever-use of 6 different antihistamines compared to controls adjusted for age at breast cancer diagnosis and TNM-stage.

Late Entry Model
Univariate Analyses

Figure 4:
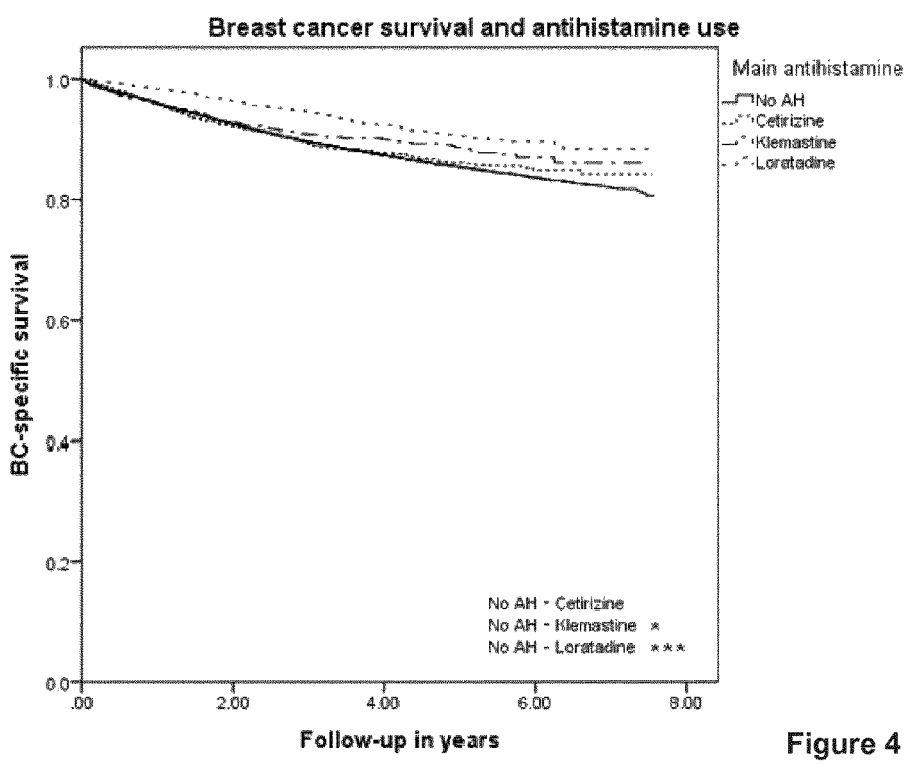
FIG. 4 is a graph showing breast cancer survival according to ever-use of antihistamines of Cetirizine, Klemastine and Loratadine in a late entry model.
Figure 5:
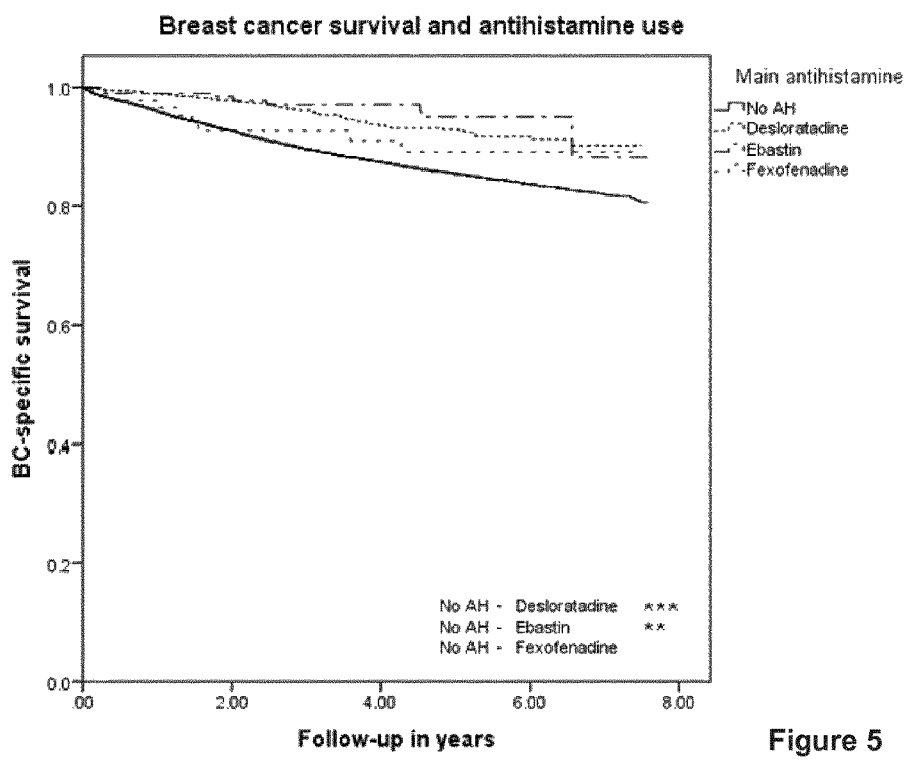
FIG. 5 is a graph showing breast cancer survival according to ever-use of antihistamines of Desloratadine, Ebastin and Fexofenadine in a late entry model.
Figure 6:
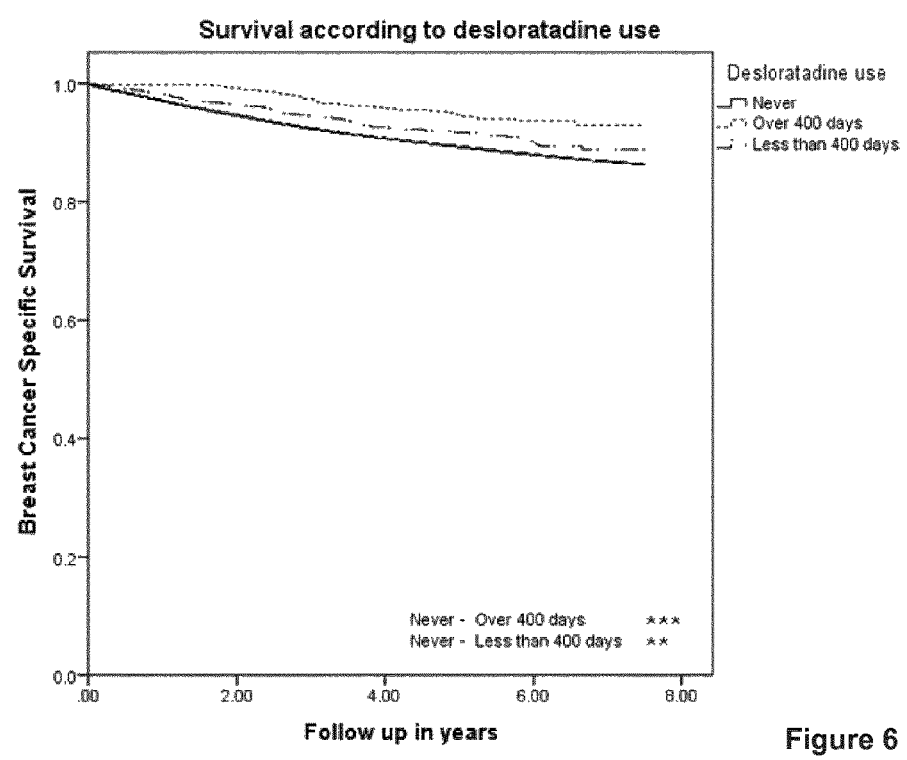
FIG. 6 is a graph showing breast cancer survival according to duration of use of desloratadine in a late entry model.
Figure 7:
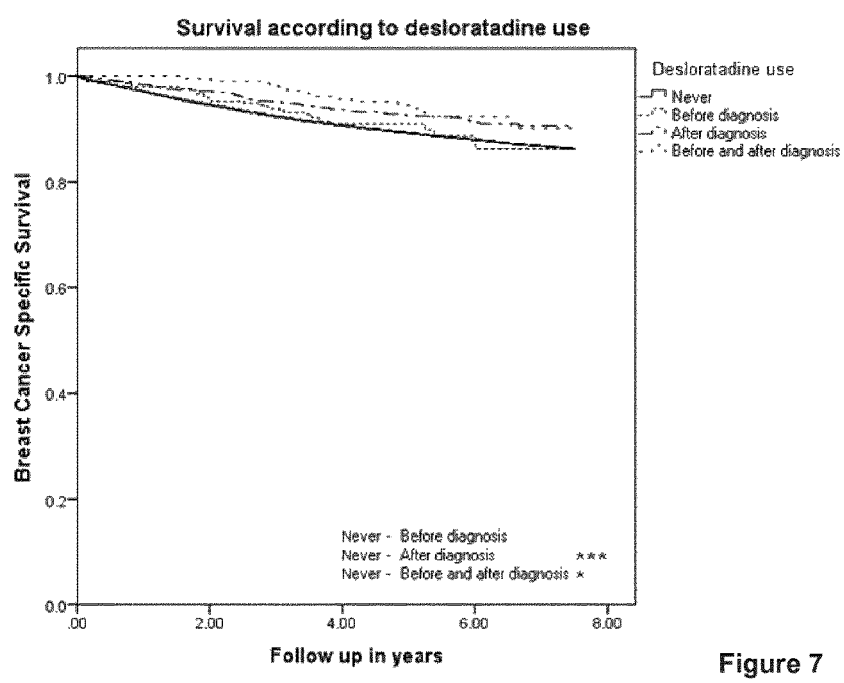
FIG. 7 is a graph showing breast cancer survival according to when the women used desloratadine in a late entry model.

Women using, loratadine, desloratadine and ebastin had a statistically significant longer BC specific survival, compared to controls. Women using cetirizine, klemastine and fexofenadine had a non-statistically significant longer BC specific survival compared to controls (FIGS. 4 and 5). FIG. 4. Breast cancer survival according to ever-use of antihistamines of Cetirizine, Klemastine and Loratadine in a late entry model. All cases before 1st of Jul. 2005 and all women with unknown N-status have been censored. N=14192 in the No AH group, N=2298 in the Cetirizine group, N=1777 in the Klemastine group and N=1745 in the Loratadine group. FIG. 5. Breast cancer survival according to ever-use of antihistamines of Desloratadine, Ebastin and Fexofenadine in a late entry model. All cases before 1st of Jul. 2005 and all women with unknown N-status have been censored. N=14192 in the No AH group, N=1338 in the Desloratadine group, N=205 in the Ebastin group and N=97 in the Fexofenadine group.

Multivariate Analyses

Table 5 shows HR for each group of antihistamine users adjusted for age at BC diagnosis and TN. Women using desloratadine had a HR of 0.69 (0.52-0.91). Loratadine users had a HR of 0.74 (0.60-0.93). Cetirizine users had a HR of 1.13 (0.96-1.33) and Klemastine users had a HR of 0.98 (0.80-1.19). Ebastin users had a HR of 0.50 (0.22-1.12) and Fexofenadine users had a HR of 0.73 (0.30-1.76). This analysis was also stratified for ER-status, but the results did not differ noticeably (data not shown).

TABLE 5

Cox proportional harzard - late entry model
Variables in the Equation

|  | B | SE | Wald | df | Sig. | Exp(B) | 95.0% Cl for Exp(B) Lower | 95.0% Cl for Exp(B) Upper |
|---|---|---|---|---|---|---|---|---|
| Age at BC diagnosis | .034 | .002 | 358.809 | 1 | .000 | 1.034 | 1.031 | 1.038 |
| T1 |  |  | 536.967 | 4 | .000 |  |  |  |
| T2 | 1.074 | .062 | 295.987 | 1 | .000 | 2.927 | 2.590 | 3.308 |
| T3 | 1.732 | .084 | 426.138 | 1 | .000 | 5.651 | 4.794 | 6.660 |
| T4 | 1.759 | .098 | 320.958 | 1 | .000 | 5.807 | 4.790 | 7.039 |
| T missing | .825 | .173 | 22.794 | 1 | .000 | 2.283 | 1.627 | 3.204 |
| N0 |  |  | 215.445 | 3 | .000 |  |  |  |
| N1 | .736 | .053 | 194.105 | 1 | .000 | 2.087 | 1.882 | 2.315 |
| N2 | .910 | .111 | 66.769 | 1 | .000 | 2.483 | 1.997 | 3.089 |
| N3 | 1.054 | .154 | 46.672 | 1 | .000 | 2.870 | 2.121 | 3.883 |
| M0 |  |  | 361.237 | 2 | .000 |  |  |  |
| M1 | 1.605 | .086 | 347.594 | 1 | .000 | 4.976 | 4.204 | 5.890 |
| M missing | −.006 | .059 | .012 | 1 | .912 | .994 | .885 | 1.115 |
| No antihistamine |  |  | 17.485 | 6 | .008 |  |  |  |
| Cetirizine | .178 | .084 | 4.506 | 1 | .034 | 1.194 | 1.014 | 1.407 |
| Klemastine | .000 | .100 | .000 | 1 | .996 | 1.000 | .821 | 1.217 |
| Loratadine | −.203 | .112 | 3.310 | 1 | .069 | .816 | .655 | 1.016 |
| Desloratadine | −.354 | .143 | 6.138 | 1 | .013 | .702 | .530 | .929 |
| Ebastine | −.615 | .410 | 2.255 | 1 | .133 | .541 | .242 | 1.207 |
| Fexofenadine | −.220 | .448 | .241 | 1 | .624 | .802 | .333 | 1.932 |

Hazard ratios for women with ever-use of 6 groups of antihistamines compared to controls adjusted for age at breast cancer diagnosis and TN-stage. All cases before 1st of Jul. 2005 and all women with unknown N-status have been censored.

TABLE 6

Cox proportional harzard - late entry model. Hazard ratios for women according to duration of use of desloratadine, adjusted for age at breast cancer diagnosis and TN-stage.
Variables in the Equation

|  | B | SE | Wald | df | Sig. | Exp(B) | 95.0% Cl for Exp(B) Lower | 95.0% Cl for Exp(B) Upper |
|---|---|---|---|---|---|---|---|---|
| Age at BC diagnosis | .036 | .001 | 1337.898 | 1 | .000 | 1.036 | 1.034 | 1.038 |
| T1 |  |  | 2057.966 | 5 | 0.000 | 1.000 |  |  |
| T2 | .949 | .040 | 569.204 | 1 | .000 | 2.582 | 2.389 | 2.791 |
| T3 | 1.550 | .056 | 756.783 | 1 | .000 | 4.710 | 4.218 | 5.260 |
| T4 | 1.924 | .059 | 1066.933 | 1 | .000 | 6.846 | 6.100 | 7.684 |
| Tis | −.962 | .081 | 141.377 | 1 | .000 | .382 | .326 | .448 |
| T missing | .121 | .049 | 6.042 | 1 | .014 | 1.128 | 1.025 | 1.242 |
| N0 |  |  | 683.655 | 4 | .000 | 1.000 |  |  |
| N1 | .833 | .037 | 514.688 | 1 | .000 | 2.299 | 2.140 | 2.471 |
| N2 | 1.146 | .095 | 145.253 | 1 | .000 | 3.145 | 2.610 | 3.789 |
| N3 | 1.355 | .130 | 109.057 | 1 | .000 | 3.876 | 3.006 | 4.998 |
| N missing | .834 | .044 | 363.880 | 1 | .000 | 2.301 | 2.113 | 2.507 |
| Never desloratadine |  |  | 7.089 | 2 | .029 | 1.000 |  |  |
| Over 400 days desloratadine | −.473 | .183 | 6.671 | 1 | .010 | .623 | .435 | .892 |
| Less than 400 days desloratadine | −.059 | .087 | .457 | 1 | .499 | .943 | .795 | 1.118 |

TABLE 7

Cox proportional harzard - late entry model. Hazard ratios for women according to when women used desloratadine, adjusted for age at breast cancer diagnosis and TN-stage.
Variables in the Equation

|  | B | SE | Wald | df | Sig. | Exp(B) | 95.0% Cl for Exp(B) Lower | 95.0% Cl for Exp(B) Upper |
|---|---|---|---|---|---|---|---|---|
| Age at BC diagnosis | .036 | .001 | 1338.520 | 1 | .000 | 1.036 | 1.034 | 1.038 |
| T1 |  |  | 2057.946 | 5 | 0.000 | 1.000 |  |  |

TABLE 7-continued

Cox proportional harzard - late entry model. Hazard ratios for women according to when women used desloratadine, adjusted for age at breast cancer diagnosis and TN-stage.
Variables in the Equation

| | B | SE | Wald | df | Sig. | Exp(B) | 95.0% CI for Exp(B) Lower | Upper |
|---|---|---|---|---|---|---|---|---|
| T2 | .949 | .040 | 569.371 | 1 | .000 | 2.582 | 2.389 | 2.792 |
| T3 | 1.551 | .056 | 757.728 | 1 | .000 | 4.715 | 4.222 | 5.265 |
| T4 | 1.924 | .059 | 1067.598 | 1 | .000 | 6.851 | 6.104 | 7.689 |
| Tis | −.962 | .081 | 141.279 | 1 | .000 | .382 | .326 | .448 |
| T missing | .122 | .049 | 6.202 | 1 | .013 | 1.130 | 1.026 | 1.244 |
| N0 | | | 683.819 | 4 | .000 | 1.000 | | |
| N1 | .833 | .037 | 514.852 | 1 | .000 | 2.300 | 2.140 | 2.471 |
| N2 | 1.143 | .095 | 144.258 | 1 | .000 | 3.135 | 2.601 | 3.777 |
| N3 | 1.356 | .130 | 109.190 | 1 | .000 | 3.880 | 3.009 | 5.003 |
| N missing | .835 | .044 | 364.620 | 1 | .000 | 2.304 | 2.115 | 2.510 |
| Never desloratadine | | | 6.983 | 3 | .072 | 1.000 | | |
| Desloratadine before diagnosis | .200 | .186 | 1.148 | 1 | .284 | 1.221 | .847 | 1.760 |
| Desloratadine after diagnosis | −.204 | .092 | 4.979 | 1 | .026 | .815 | .681 | .975 |
| Desloratadine before and after diagnosis | −.235 | .259 | .828 | 1 | .363 | .790 | .476 | 1.312 |

TABLE 8

ER Negative Breast Cancer - late entry model. Hazard ratios for women according to breast cancer ER molecular subtype, adjusted for age at breast cancer diagnosis and TN-stage. Women using desloratadine had a HR of 0.60 (0.45-0.81).
Variables in the Equation

| | B | SE | Wald | df | Sig. | Exp(B) | 95.0% CI for Exp(B) Lower | Upper |
|---|---|---|---|---|---|---|---|---|
| Age at BC diagnosis | .027 | .002 | 277.120 | 1 | .000 | 1.028 | 1.025 | 1.031 |
| Tconv | | | 766.748 | 4 | .000 | | | |
| Tconv(1) | 1.271 | .072 | 311.734 | 1 | .000 | 3.564 | 3.095 | 4.103 |
| TconV(2) | 1.737 | .096 | 326.802 | 1 | .000 | 5.678 | 4.704 | 6.855 |
| Tconv(3) | 2.217 | .101 | 482.971 | 1 | .000 | 9.178 | 7.531 | 11.184 |
| Tconv(4) | .009 | .090 | .009 | 1 | .924 | 1.009 | .845 | 1.204 |
| Nconv | | | 326.017 | 4 | .000 | | | |
| Nconv(1) | 1.131 | .066 | 296.048 | 1 | .000 | 3.100 | 2.725 | 3.526 |
| NconV(2) | 1.359 | .147 | 85.344 | 1 | .000 | 3.892 | 2.917 | 5.192 |
| Nconv(3) | 1.472 | .207 | 50.761 | 1 | .000 | 4.356 | 2.906 | 6.530 |
| Nconv(4) | .714 | .083 | 74.026 | 1 | .000 | 2.041 | 1.735 | 2.402 |
| Cetirizin | .400 | .078 | 25.949 | 1 | .000 | 1.491 | 1.279 | 1.739 |
| Klemaslin | .246 | .094 | 6.835 | 1 | .009 | 1.279 | 1.064 | 1.539 |
| Loraladin | −.057 | .103 | .304 | 1 | .581 | .945 | .773 | 1.156 |
| Desloratadin | −.506 | .147 | 11.777 | 1 | .001 | .603 | .451 | .805 |
| Ebastin | −.219 | .291 | .566 | 1 | .452 | .804 | .454 | 1.421 |
| Fexofenadin | −1.153 | .579 | 3.967 | 1 | .046 | .316 | .102 | .982 |

TABLE 9

ER Positive Breast Cancer - late entry model. Hazard ratios for women according to breast cancer ER molecular subtype, adjusted for age at breast cancer diagnosis and TN-stage. Women using desloratadine had a HR of 0.62 (0.51-0.75).
Variables in the Equation

| | B | SE | Wald | df | Sig. | Exp(B) | 95.0% CI for Exp(B) Lower | Upper |
|---|---|---|---|---|---|---|---|---|
| Age at BC diagnosis | .039 | .001 | 1074.232 | 1 | .000 | 1.040 | 1.038 | 1.042 |
| Tconv | | | 916.224 | 4 | .000 | | | |
| Tconv(1) | .812 | .047 | 302.089 | 1 | .000 | 2.252 | 2.055 | 2.468 |
| TconV(2) | 1.405 | .068 | 427.535 | 1 | .000 | 4.076 | 3.567 | 4.656 |
| Tconv(3) | 1.741 | .071 | 594.017 | 1 | .000 | 5.705 | 4.960 | 6.563 |

TABLE 9-continued

ER Positive Breast Cancer - late entry model. Hazard ratios for women according to breast cancer ER molecular subtype, adjusted for age at breast cancer diagnosis and TN-stage. Women using desloratadine had a HR of 0.62 (0.51-0.75).
Variables in the Equation

|  | B | SE | Wald | df | Sig. | Exp(B) | 95.0% CI for Exp(B) Lower | Upper |
|---|---|---|---|---|---|---|---|---|
| Tconv(4) | .218 | .059 | 13.590 | 1 | .000 | 1.244 | 1.108 | 1.397 |
| Nconv |  |  | 477.143 | 4 | .000 |  |  |  |
| Nconv(1) | .769 | .044 | 302.308 | 1 | .000 | 2.157 | 1.978 | 2.352 |
| NconV(2) | 1.139 | .117 | 95.226 | 1 | .000 | 3.123 | 2.484 | 3.925 |
| Nconv(3) | 1.415 | .156 | 81.835 | 1 | .000 | 4.117 | 3.030 | 5.594 |
| Nconv(4) | .982 | .054 | 332.528 | 1 | .000 | 2.669 | 2.402 | 2.966 |
| Cetirizin | .773 | .054 | 205.458 | 1 | .000 | 2.166 | 1.949 | 2.407 |
| Klemaslin | .420 | .062 | 45.177 | 1 | .000 | 1.521 | 1.346 | 1.719 |
| Loratadin | .084 | .076 | 1.222 | 1 | ..269 | 1.087 | .937 | 1.262 |
| Desloratadin | −.484 | .098 | 24.490 | 1 | .000 | .616 | .509 | .747 |
| Ebastin | −.594 | .237 | 6.268 | 1 | .012 | .552 | .347 | .879 |
| Fexofenadin | −.191 | .290 | .431 | 1 | .511 | .826 | .468 | 1.460 |

Using an extended breast cancer material of all cases from the Swedish Cancer Registry 2000-2013 (n=103 500 cases) linking the data with the Drug Prescription Registry, a replication study was carried out, as shown in table 10. Due to the large number of cases, a higher resolution is achieved, confirming the better overall and BC specific survival for users of desloratadine or ebastin compared with non-users.

TABLE 10

Breast cancer survival and overall survival adjusted for age and divided into two time periods 2005-2008 and 2009-2013. Use of different antihistamines after diagnosis in relation to tumour stage. Late entry models.

|  | Breast cancer survival | | Overall survival | |
|---|---|---|---|---|
|  | HR | 95% confidence interval | HR | 95% confidence interval |
| Survival 2005-2008 |  |  |  |  |
| Stage 1 | 1.0 |  | 1.0 |  |
| Stage 2 | 4.98 | 3.57-6.95 | 3.37 | 2.70-4.22 |
| Stage 3 | 12.76 | 9.00-18.07 | 6.82 | 5.34-8.72 |
| Stage 4 | 45.93 | 32.20-63.52 | 22.55 | 18.07-28.14 |
| Cetirizine | 1.08 | 0.81-1.44 | 1.41 | 1.15-1.74 |
| Clemastine | 1.43 | 1.09-1.87 | 2.07 | 1.72-2.49 |
| Loratadine | 0.77 | 0.54-1.14 | 1.05 | 0.80-1.37 |
| Desloratadine | 0.47 | 0.28-0.79 | 0.47 | 0.31-0.72 |
| Ebastine | 0.25 | 0.04-1.80 | 0.48 | 0.16-1.51 |
| Fexofenadine | 1.20 | 0.39-3.75 | 1.40 | 0.58-3.37 |
| Survival 2009-2014 |  |  |  |  |
| Stage 1 | 1.0 |  | 1.0 |  |
| Stage 2 | 3.60 | 3.16-4.11 | 2.36 | 2.17-2.59 |
| Stage 3 | 8.63 | 7.46-9.99 | 4.82 | 4.34-5.3 |
| Stage 4 | 35.37 | 30.68-40.77 | 15.97 | 14.34-17.78 |
| Cetirizine | 1.21 | 1.06-1.39 | 1.09 | 0.97-1.22 |
| Clemastine | 0.94 | 0.80-1.10 | 1.08 | 0.96-1.21 |
| Loratadine | 0.93 | 0.78-1.11 | 0.86 | 0.75-0.99 |
| Desloratadine | 0.74 | 0.60-0.91 | 0.71 | 0.61-0.84 |
| Ebastine | 0.75 | 0.46-1.23 | 0.91 | 0.65-1.27 |
| Fexofenadine | 0.85 | 0.40-1.78 | 0.65 | 0.34-1.25 |

Looking at the years before 2009 the survival is greatly improved for desloratadine users compared with non users HR=0.63. The overall effect for better breast cancer survival with desloratadine is summarized in table 11. It is also of great interest to note that cetirizine and clemastine negatively affects survival.

TABLE 11

Summary of breast cancer survival at use of desloratadine for one year (late entry model).

| Desloratadine use | N | HR | 95% CI |
|---|---|---|---|
| ≥400 days | 597 | 0.62 | 0.44-0.89 |
| <400 days | 2030 | 0.94 | 0.80-1.10 |
| Never | 51779 | 1.00 |  |

The invention claimed is:

1. A method of treating breast cancer in a patient diagnosed with breast cancer, the method consisting of administering to the patient an effective amount of desloratadine, wherein the breast cancer is selected from the group consisting of positive and negative ER, PR, her2 breast cancer molecular subtypes, and invasive breast carcinomas, and wherein the patient is not diagnosed with a seasonal allergic condition.

2. The method of claim 1, wherein the breast cancer is selected from the group consisting of positive and negative ER invasive breast carcinomas.

3. The method of claim 1, wherein the treatment is continuous for at least 50 days.

4. The method of claim 1, wherein said treatment improves the prognosis for the patient diagnosed with breast cancer.

5. The method of claim 1, wherein said treatment increases the survival time for the patient diagnosed with breast cancer.

6. The method of claim 1, wherein the daily dose of the desloratadine corresponds to the defined daily dose (DDD).

7. The method of claim 1, wherein the dose of the desloratadine is between 2.5 to 45 mg per day.

8. The method of claim 1, wherein the dose of the desloratadine is between 45 to 250 mg per day.

9. The method of claim 1, wherein the patient is perioperational.

* * * * *